United States Patent
Bonnin et al.

(10) Patent No.: US 7,186,984 B2
(45) Date of Patent: Mar. 6, 2007

(54) METHOD FOR QUANTIFYING THE RADIOACTIVITY OF LIVING STRUCTURES OF SMALL DIMENSIONS BY EMPLOYING EMISSION TOMOGRAPHY

(75) Inventors: Maleaume Bonnin, Toulouse (FR); Jean-Paul Esquerre, Castanet Tolosan (FR); Pierre Gantet, Toulouse (FR); Pierre Payoux, Aucamville (FR)

(73) Assignee: Segami, Paris (FR)

( * ) Notice: Subject to any disclaimer, the term of this patent is extended or adjusted under 35 U.S.C. 154(b) by 78 days.

(21) Appl. No.: 11/098,970

(22) Filed: Apr. 5, 2005

(65) Prior Publication Data

US 2006/0054827 A1    Mar. 16, 2006

(30) Foreign Application Priority Data

Apr. 5, 2004    (FR) .................. 04 50678

(51) Int. Cl.
*G01T 1/20*    (2006.01)
(52) U.S. Cl. .................................... 250/369
(58) Field of Classification Search ................ 250/369
See application file for complete search history.

(56) References Cited

OTHER PUBLICATIONS

V. Frouin et al., "Correction of partial-volume effect for PET stratal imaging: fast implementation and study of robustness", 2002, Journal of Medicine, vol. 43(12), pp. 1715-1726.*

* cited by examiner

*Primary Examiner*—David Porta
*Assistant Examiner*—Marcus Taningco
(74) *Attorney, Agent, or Firm*—Fulbright & Jaworski LLP

(57) ABSTRACT

The invention relates to a process of quantification of the radioactivity of living tissue structures by emission tomography to determine the concentration of a radioactive tracer. It includes the acquisition of images in three dimensions, the determination of the point dispersion function of the imaging system, its convolution with a high-resolution model to obtain a low resolution model, a readjustment, an appraisal of the match between the low-resolution model and the images, in case of a negative test, iterative steps of deformation of the high-resolution model and of performing the preceding steps until the test remains negative, the segmentation of the images into regions, the calculation of the activity of the regions, the determination of a geometrical transfer matrix, its inversion and the multiplication, so as to obtain data for correction of the partial volume effect. The point dispersion function is obtained by a calibration process resorting to a test object called "anthropomorphic phantom" and the quantification of the radioactivity of the compartments of this object.

17 Claims, 5 Drawing Sheets

METHOD FOR QUANTIFYING THE RADIOACTIVITY OF LIVING STRUCTURES OF SMALL DIMENSIONS BY EMPLOYING EMISSION TOMOGRAPHY

BACKGROUND OF THE INVENTION

This application claims priority from FR 04 50678 filed Apr. 5, 2004, herein incorporated by reference in its entirety.

FIELD OF THE INVENTION

The invention relates to a method for quantifying the radioactivity of structures of a live tissue of small dimensions by employing emission tomography.

It is first of all useful to recall the chief characteristics of emission tomography.

Emission tomography is an imaging technique making it possible to visualize the distribution of a radioactive tracer inside of an organism, a human organism for example. It includes tomographie par émission monophotonique (or "TEMP") and tomographie par émission de positrons (or "TEP") (which according to English-language terminology are currently called "SPECT" for "single photon computerized tomography" or "PET" for "positron emission tomography"), respectively. Beyond the ability of such a system to form an image, it is increasingly sought in order to be able to measure the radioactivity present in a particular region of the volume explored, which hereinafter shall be called simply "activity." In a case where the size of this region is close to the spatial resolution of the system being investigated, the quantification becomes imprecise: the volumetric activity is systematically underestimated and it is difficult to separate the activities coming from two neighboring regions. This phenomenon, called "partial volume effect" is notably present in the case of measuring the radioactivity contained in structures of small size, known by the name of "striata," in the imaging of dopaminergic neurotransmission.

The problem of quantification in SPECT and PET has been the object of much research. The number of works published in this domain witnesses both the difficulties in obtaining a precise quantification of radioactivity by means of these imaging systems and the increasing importance of having mathematical values.

It is well known that the quality of SPECT and PET images is degraded by various physical phenomena. The self-attenuation of photons might be mentioned, the so-called "Compton" diffusion, a limited and spatially varying spatial resolution, as well as the so-called "partial volume effect" or "PVE."

In the known art an attempt has been made to alleviate these problems, and several processes and techniques are today available for correcting or, at least, trying to compensate for these phenomena.

Classically, the necessary corrections are applied to the sequential way by considering that phenomena independent of one another are involved.

The present invention finds particular application in the correction of the effect called "partial volume effect," which hereinafter shall be called the PVE for the sake of simplification. Indeed, this is the most punishing phenomenon when it is desired to quantify the radioactivity in structures of small size, like the striata previously mentioned. This phenomenon is described, for example, in the article by M. Soret et al., entitled: "Quantitative accuracy of dopaminergic neurotransmission imaging with (123) SPECT" which appeared in the "Journal of Nuclear Medicine" 2003, vol. 44(7), pages 1184–1193.

PVE is due to the low resolution of the images (typically 4 to 12 mm, depending on the imaging system used) compared to the size of the volumes of the different tissues whose radioactivity was to be measured. For example, between a "caudate" and a "putamen" the space is close to 2 mm at certain places. Moreover, what is involved is structures of flattened shapes whose thickness is but a few millimeters per point. The activity measurements in one of these structures are therefore influenced by the activities of nearby structures. The problem is all the greater when there is a great difference in activity between the structures.

In the known art, various approaches have been proposed for correcting the PVE. They can be classified in three main categories:

i. Processes based on the determination of a "recovery coefficient" in the English terminology currently in use. As a non-limiting example, Such a process is described in the article of E. Hoffman et ail., entitled: "Quantification in Positron emission computed tomography. 1. Effect of object size," appearing in "Journal of Computer Assisted Tomography," 1979, vol. 3, pages 299–308;

ii. Processes based on the modeling of temporal dynamic series. By way of non-limitative example, such a process is described in the article of H. Iida et al., entitled, "Quantification of regional cerebral blood flow corrected for partial volume effect using O-15 water and PET: I. Theory, error analysis, and stereologic comparison" which appeared in: "Journal of Cerebral Blood Flow & Metabolism," 2000, vol. 20(8), pages 1237–1251; and iii. Processes using another modality of imaging which permits obtaining anatomical information a priori.

These processes are not free of problems.

Indeed, processes of the first type (i.) making it possible to take into account the partial volume effect or PVE in the case of spherical objects, but are not appropriate in the case of more or less complex structures, particularly when it is a case of the "striata" mentioned above.

The processes of the second type (ii) assume that a dynamic set of data is available, which is not the case in the majority of studies of dopaminergic neurotransmission performed at equilibrium.

The processes for correcting the PVE using anatomical information a priori (processes of the third type iii.) give the most interesting results.

Some of these processes employ algorithms of the "pixel-by-pixel" type ("APA" for "anatomically guided pixel-by-pixel algorithms" in the currently used English terminology).

The pixel-by-pixel type algorithms consist in the first place of labeling segmented anatomical images by attributing an arbitrary value to each pixel according to the region to which they belong. A convolution is then performed on the volume thus defined by the function called "point dispersion" of the imaging system used, in order to constitute a degraded anatomical model. The initial volume is then divided, vowel by vowel, by this degraded anatomical model, so that the volumetric activity present in each, vowel corresponds more to the real concentration. Practically, these algorithms are used only for cerebral perfusion examinations.

For more detailed explanation of these processes, it may help to refer to the article of C. Meltzer et al., entitled, "Correction of PET in the partial volume effects in human cerebral cortex by MR imaging," appearing in: "Journal of Computer Assisted Tomography," 1990, vol. 14(4), pages 561–570.

Other processes employ algorithms based on a matrix method.

These algorithms are also based on the segmentation of an anatomical volume from MRI (magnetic resonance imaging) images. A convolution of the anatomical reference thus obtained by the function called "point dispersion function" or PDF of the imaging system used, in order to estimate the contamination of the regions by one another. This contamination is modeled in the form of a matrix wherein each of the coefficients corresponds to the participation of the activity of one region in the activity of other regions. It is then sufficient to invert this matrix to correct the partial volume effect.

For a more detailed explanation of these processes it may help to refer to the article of O. Rousset et al., entitled: "Correction for partial volume effect in PET: principles and validation," appearing in "Journal of Nuclear Medicine," 1998, vol. 39(5), pages 904–911.

Practically speaking, these algorithms are the only ones presently in use for satisfactorily correcting the EVP for the quantification of the striata in imaging of dopaminergic neurotransmission, whether in PET or SPECT."

For images of the PET type it might be advantageous to refer to the article of V. Frouin et al., entitled: "Correction of partial-volume effect for PET stratal imaging: fast implementation and study of robustness: appearing in "Journal of Nuclear Medicine," 2002, vol. 43(12), pages 1715–1726.

For images of the SPECT type one might refer advantageously to the previously cited article of Soret et al.

However, it is to be noted that these processes have been employed on virtual or physical test objects. The use of these techniques in current practice, for example in a hospital setting, has not yet been published.

The problem that now presents itself for being able to make a precise quantification of the strata in a hospital setting is taking into account the partial volume effect or PVE. Indeed, this correction requires having high resolution anatomical information on the structures to be quantified, whereas in general the patient examined, either has not previously been subjected to an IRM examination, or his IRM images have not been segmented so as to be able to isolated the striata.

Furthermore, the PVE correction requires a precise knowledge of the aforesaid function called "point dispersion" connected to the imaging system used, or called PDF hereinafter. Furthermore the PVE correction requires the precise knowledge of the point dispersion function (PDF) of the imaging system. Now, it happens that, in current practice, the calibration of an imaging system and the measurement of its PDF after reconstruction, on a volume of three dimensions, hereinafter called "3D," are generally performed with the aid of a simple geometry source such as a point source or a "line" source as described in M. Soret's article cited above. Now, taking into account the spatial resolution (comprised between 8 and 12 mm in SPECT) and of the sampling pitch (classically near 2.5 mm per pixel) it is hard to determine the PDF with precision. Moreover, the convergence of the iterative reconstruction algorithms depends on the complexity of the object. The resolution measured with a line source may be quite different from the resolution in a clinical situation. Now, an error in the determination of the real PDF involves a correction of the erroneous PVE, and an imprecise qualtification. A method of calibration of the full chain of measurement must therefore be employed, so that this calibration will reflect a real clinical situation as much as possible.

SUMMARY AND OBJECTS OF THE INVENTION

The invention aims to satisfy the needs which are felt in the field of the quantification of the radioactivity of living structures of small dimensions employing tomography by emission, and to remedy the problems of the processes of the known art, some of which have been recalled.

In particular it permits an effective correction of the effect called, "the partial volume effect" or PVE.

The invention permits performing a quantification of the striata in SPECT or PET imaging, in a real situation, in a hospital environment, for example. The invention permits a trustworthy quantification without the need to have segmented MRI (magnetic resonance images) as some processes of the prior art require. The entire measurement chain, including a detection device and a data processing unit, is calibrated with the aid of a test object representing a real clinical situation.

According to an important characteristic, the invention uses a high-resolution 3D virtual model of striata which shall be considered "deformable."

This model is used as an a priori anatomical form for the correction of the partial volume effect or PVE. A convolution step is then performed on this model for the PDF of the measuring chain to obtain a "degraded" model having a form close to that which should be the SPECT or PET of the model. The "degraded model" is then recalculated on the SPECT or PET images of a real structure of living tissues, for example those associated with a patient. The model is then "deformed" such that the degraded version of the model best coincides with the image of the striata in SPECT or PET. A geometrical transfer matrix is obtained by calculating, for the deformed model, the respective contribution of each structure forming the striatum in the nearby structures of the deformed model degraded. The deformed model, degraded and readjusted makes it possible to define the areas of interest in the SPECT or PET images. The activities contained in each of these zones are the uncorrected PVE activities.

Correction of the PVE is finally obtained by matrix multiplication between the above-mentioned geometrical transfer matrix, after inversion, and the uncorrected values.

In a preferred variant embodiment, the detection and treatment chain is calibrated by employing a complex physical object or test object which best reproduces a clinical situation in the imaging of the striata. This test object is generally known by the name, "anthropomorphic phantom." Such a test object is manufactured, for example, by Radiology Support Devices (RSD), 1904 East Dominguez St., Long Beach, Calif. (USA) 90610. It typically comprises four compartments, corresponding to the striata, which can be filled, and a compartment for the rest of the brain. Each compartment is filled with a known amount of radioactivity. The acquisition of the images of this test object is performed according to the regular protocol for performing PET or SPECT neurotransmission examinations. A tomodensitometry by X radiation of this "calibration phantom," then a segmentation of the structures hereinabove, make it possible to know the exact morphology of the "calibration phantom." The result of this segmentation is used as a morphological "a priori" for the quantification on the SPECT or PET images of this "calibration phantom." In a practical way, the calibration step consists in finding a PDF and a sensitivity factor to use in the PVE correction to restore insofar as possible the real activities injected into the phantom.

The invention therefore has as its chief object a process of quantification of the radioactivity of an assembly of living tissue structures so as to determine the concentration of a radioactive tracer in these living tissue structures by means of an imaging system comprising a chain of detection and employing tomography called "emission tomography," the process described comprising an initial stage of acquisition and reconstruction of a plurality of three-dimensional images by the said imaging detection chain from the said living structures and their storage in the form of numerical data in memory means, characterized in that it comprises at least:

a step of generation of a high-resolution generic numeric anatomical model of a form close to that of the said assembly of the living structures to be quantified, and its storage in the form of numerical data in memory means;

a step of determining a function known as "point dispersion" of the said detection chain and the storage of parameters characterizing this function in the form of numerical signals in the memory means;

a step of convolution of the said generic high-resolution model with the parameters of the said point dispersion function so as to obtain a low-resolution model of the said high-resolution model and its storage internal combustion engine the form of numerical data in memory mans of the result of the said convolution;

a step of readjustment between the said plurality of images in three acquired dimensions and the said low resolution model;

a step of estimating the match between the said plurality of three-dimensional images and the said low-resolution model, followed by a step of testing by comparison with the predetermined threshold values;

as a result of a negative test, iterative steps comprising the deformation of the said high-resolution generic anatomical numerical model, its storage in the form of numerical data in memory means, and the repetition of the said steps of convolution, resetting, estimation and testing until the said test is positive;

as a result of a positive test, a step of the segmentation of the said low-resolution model in regions superimposed on the data of the said plurality of images in three dimensions;

a step of determining the radioactivity in the said plurality of images in three dimensions in the said segmented regions and storage in the form of numerical data in memory means of the results of the said determination;

a step of inverting the said geometrical transfer matrix and multiplying it by the said numerical data representing the radioactivity of the said segmented regions, so as to obtain data for correction of the so-called "partial volume" effect associated with the said living tissue structures being quantified; and a step of displaying on a visualization unit and/or a unit for storing quantification data of the said radioactive distribution within the said living tissue structures.

BRIEF DESCRIPTION OF THE DRAWINGS

The invention will now be described in greater detail in connection with the annexed drawings, among which.

DESCRIPTION OF THE EMBODIMENTS

The process of the invention will now be described in connection with FIGS. 1 to 6.

In these figures the identical elements and/or steps bear the same reference numbers and will be redescribed only as necessary.

Figure 1:
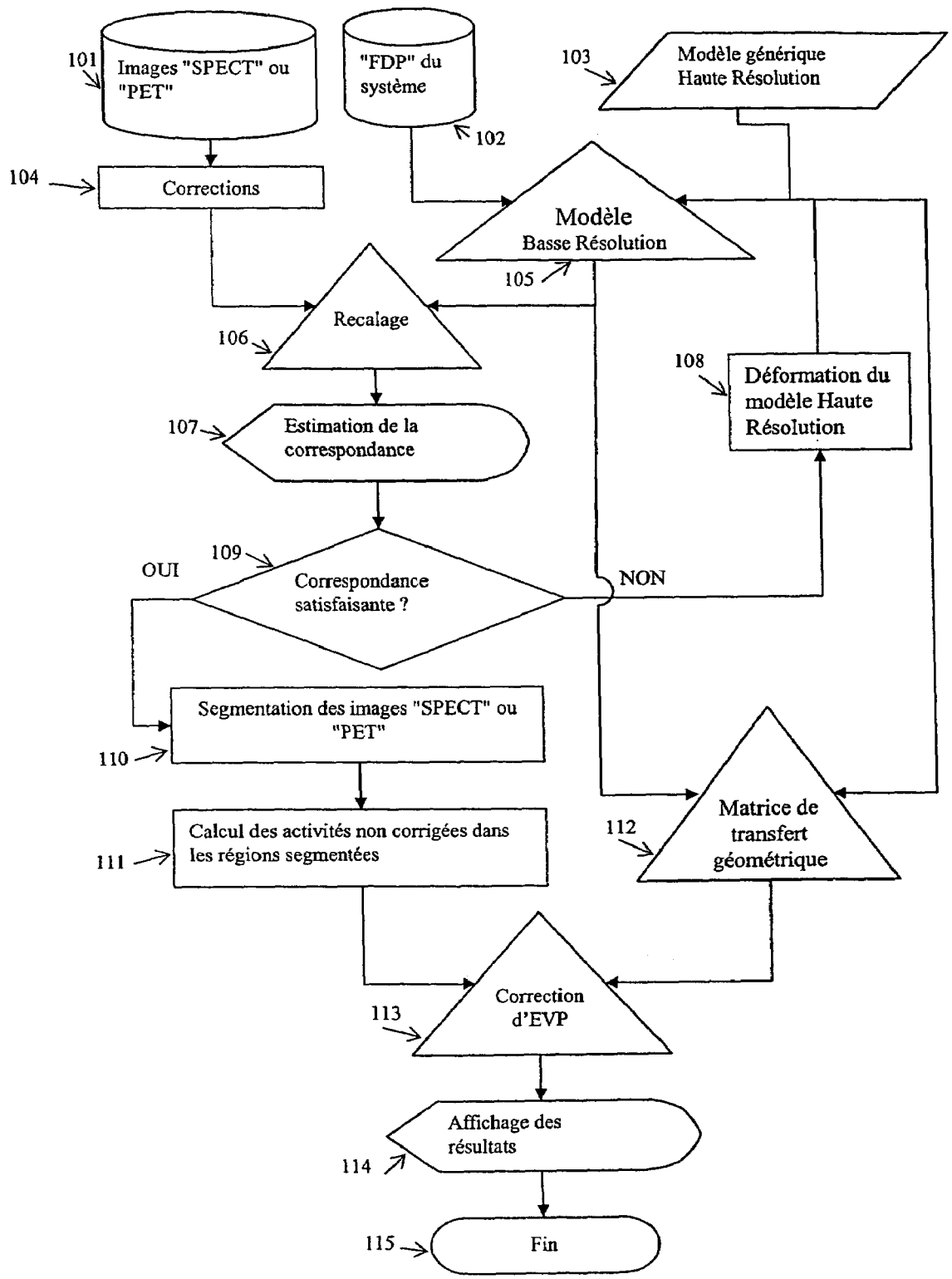
FIG. 1 is a diagram diagramming the principal steps of the method of the invention in a preferred embodiment.

FIG. 1 is a diagram showing schematically the principal steps of the method of the invention according to a preferred embodiment, this method making it possible to evaluate the radioactivity contained in structures of living tissue, i.e., to quantify them beginning from 3D images of the SPECT or PET type, for example a particular organ of a patient, and lastly to obtain a correction of the PEV of the system of imaging employed.

The first step, under the reference 101, consists of acquiring three-dimensional or 3D image s of structures of living tissues, for example those of a patient's organ, by means of a system of imaging of the SPECT or PET type. These images, which will be called "SPECT or PET VOLUME" digitized and are stored in a memory of a numerical data processing system by programs recorded, for example, on a hard disk.

The second step, 104, consists in the application of corrections to these images as needed. These corrections, classical in themselves, and well known to the man of the art, are made according to the rules of the art. They concern certain physical phenomena in connection with resolution, attenuation, artifacts, etc.

In themselves, these two first steps are common to the known art.

According to a first important characteristic, to arrive at the desired quantification, the method of the invention resorts to a high-resolution generic anatomical digital model (typically a resolution lower than or equal to 2 mm) of a shape close to that of the aforementioned organ to be quantified. This model is generated by data processing means (not represented) at the step marked 103 and stored in a memory (for example on the hard disk mentioned above).

At the stop marked 102, the point dispersion function or PDF of the detection and processing chain used, i.e., the imaging system used, is determined. As before, the parameters characterizing the PDF are stored in forms of numerical signals in the memory means (for example on the hard disk mentioned before). A process for determining these parameters will be explained as follows in connection with the description of the diagram of FIG. 3.

In the step marked 105, a convolution is performed of the high-resolution generic model generated at step 103 with the parameters of the PDF determined in step 102. This step permits obtaining a low-resolution model (about 10 mm in SPECT, and about 5 mm in PET) corresponding to the image which would be given by the imaging system of the high-resolution model.

As before, the model is stored in the memory means (for example on the hard disk mentioned before). Likewise, in what follows, unless otherwise specified, the results of-the operations relative to the successive steps are stored in memory means, which can be the same as those previously pointed out, or independent means, without the need of repetition.

In step 106, a readjustment is performed between the images acquired in step 103, SPECT or PET after any corrections in step 104, and the low-resolution model obtained in step 105. This readjustment advantageously comprises three translations and three rotations. The method used to do this readjustment can be either manual or automatic. In the former case one may resort, for example, to a visualization unit displaying the progression of the successive readjustments and of control means (control buttons etc.) on which an operator acts. In the second case, a recorded numerical data processing system can be employed to perform the operations automatically under the management of a specialized program.

The quality of the match between the SPECT and PET images, corrected as needed, at the output from step 104, and the low-resolution model of step 105, is then estimated in step 107. This estimation can be performed either automatically, in a manner well-known in itself, by taking into account a numerical criterion of distance between the two images, either manually or by visual observation.

In the first case, the estimation can be performed with the aid of a numerical data processing system in a recorded program, this operation being performed under a special program, as for example the system used for step 106 when the latter is performed automatically.

In the second case, a display unit can also be used.

According to the result of this estimation, and according to an important feature of the method of the invention, a decision is made, at the step marked 102, as to whether it is necessary in step 109 to deform the model (branch marked YES in FIG. 1) or unnecessary (branch marked NO). This decision can be made preferably by the employment of the recorded numerical data processing system mentioned above.

In case the match is not optimum or at least judged insufficient (branch marked NO in FIG. 1), the high-resolution model undergoes a deformation at the step reference 108, according to one of the most important features of the process of the invention.

This deformation may be, for example, a shift or a rotation of the images of the individual structures in relation to one another.

Figure 2A:
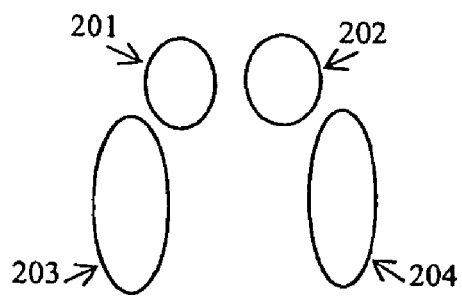
FIG. 2A shows schematically anatomical model used in the process of FIG. 1.

To be more concrete, FIG. 2A shows by way of example four structures marked 201 to 204, representing a greatly simplified anatomical model.

Figure 2B:
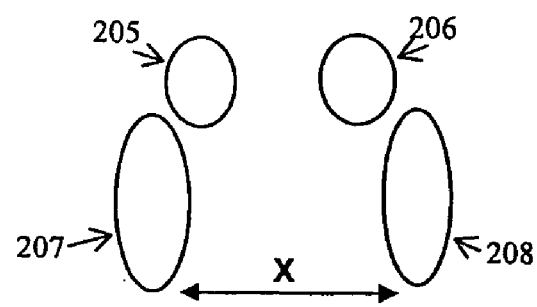
FIGS. 2B and 2C show schematically examples of the deformation of the model of FIG. 2A.

Still by way of example, FIG. 2B illustrates a first possible deformation of the model of FIG. 2A, viz., a shift along an axis X. The respective pairs of structures, 201–203, on the one hand, and 202–204 on the other, are moved apart from one another to become 205–207 and 206–208, respectively.

Figure 2C:
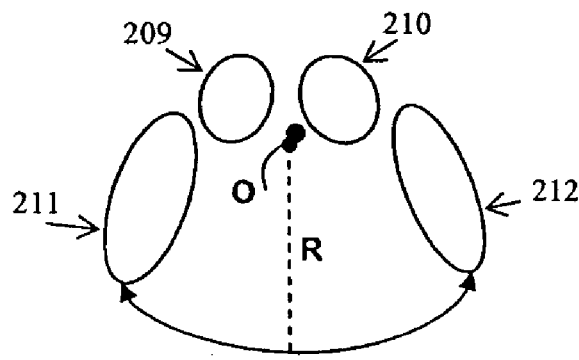

Likewise, FIG. 2C illustrates a second possible deformation of the model of FIG. 2A, viz., a rotation. The pairs of structures 201–203 and 202–204 referred to above, become 209–211 and 210–212, respectively, after a rotation of structures 203 and 204 (211 and 212 after rotation) on a circle with center O and radius R.

Other types of deformation are of course possible, including complex deformations combining translations and rotations.

The deformed model then replaces the initial high resolution. This deformed model is stored in the above-mentioned memory means and the steps previously described, 105 to 107, are repeated until a maximum match between the low-resolution model of step 105 and the SPECT or PET data, corrected if necessary, are stored at the output of step 104.

As it has been indicated, the match is judged satisfactory when the differences between the two models become less than pre-established thresholds.

Once the form of the optimized model (branch marked YES in FIG. 1), the structures of the low-resolution model of step 105 are superimposed on the data of SPECT or PET images available at the output from step 104, so as to define regions of interest on these SPECT or PET images. This operation, constituting a segmentation, is performed at the step marked 110 and the data characterizing regions of interest are stored in the memory means.

These regions of interest make it possible to calculate non-corrected activities of the PVE and to store the resultant data. This operation is performed at step 111.

A comparison between the high-resolution model available at the output of step 102, possibly deformed at step 108, and the low-resolution model available at the output from step 105, makes it possible to deduce a so-called geometric transfer to the step marked 112 from the high- and low-resolution models.

The correction of the PVE, made at the step marked 113 is then performed classically by multiplying the geometric transfer matrix, after inversion, by the uncorrected data stored at the output of step 111.

The results, which may be either activity reports (relative values) among areas of interest, or absolute values, are then displayed at step marked 114 on a visualization unit (not shown in FIG. 1) and/or recorded in a file (in the above-mentioned memory means, for example) at step 115 (end of process), for a further processing of data obtained, for example (printing, etc.).

A description will now be given of the determination of the PDF of step 102 according to a preferred embodiment, by referring to the diagram in FIG. 3.

This determination is made by a calibration process which uses a test object generally known by the term, "anthropomorphic phantom," constituted by an assemblage of various materials whose form and density characteristics are considered to reproduce those of the live tissues, as was recalled in the preamble of the present description. The geometric characteristics of this "anthropomorphic phantom" are close to a real clinical situation.

This test object classically includes several compartments which can be filled with various known radioactivities. This first operation is carried out in the step marked 301.

The test object is placed in the detection field of a SPECT or PET imaging camera (not represented). An acquisition in a tomographic mode is made, and then the images acquired are reconstructed according to classical reconstruction algorithms and the data corresponding to these images are stored in the memory means. This second operation is performed at step 302.

The reconstructed volume is then treated, at step 303, by a quantification process according to the invention. To do this, the steps 101 to 114 in FIG. 1 of the process of the invention. The only differences are the following:

In the calibration process, the high-resolution generic anatomical model of step 103 (FIG. 1) is replaced with the exact anatomical model of the real test object. Advantageously, this model can be obtained by segmenting tomodensitometric images "X" of the test object.

The test for adequacy between the data and the model (step 109 of FIG. 1) always gives a positive answer (the YES branch in FIG. 1). The possibility of deformation of the model (step 108) is therefore not used. The comparison step 109 of FIG. 1 is therefore useless.

Figure 3:
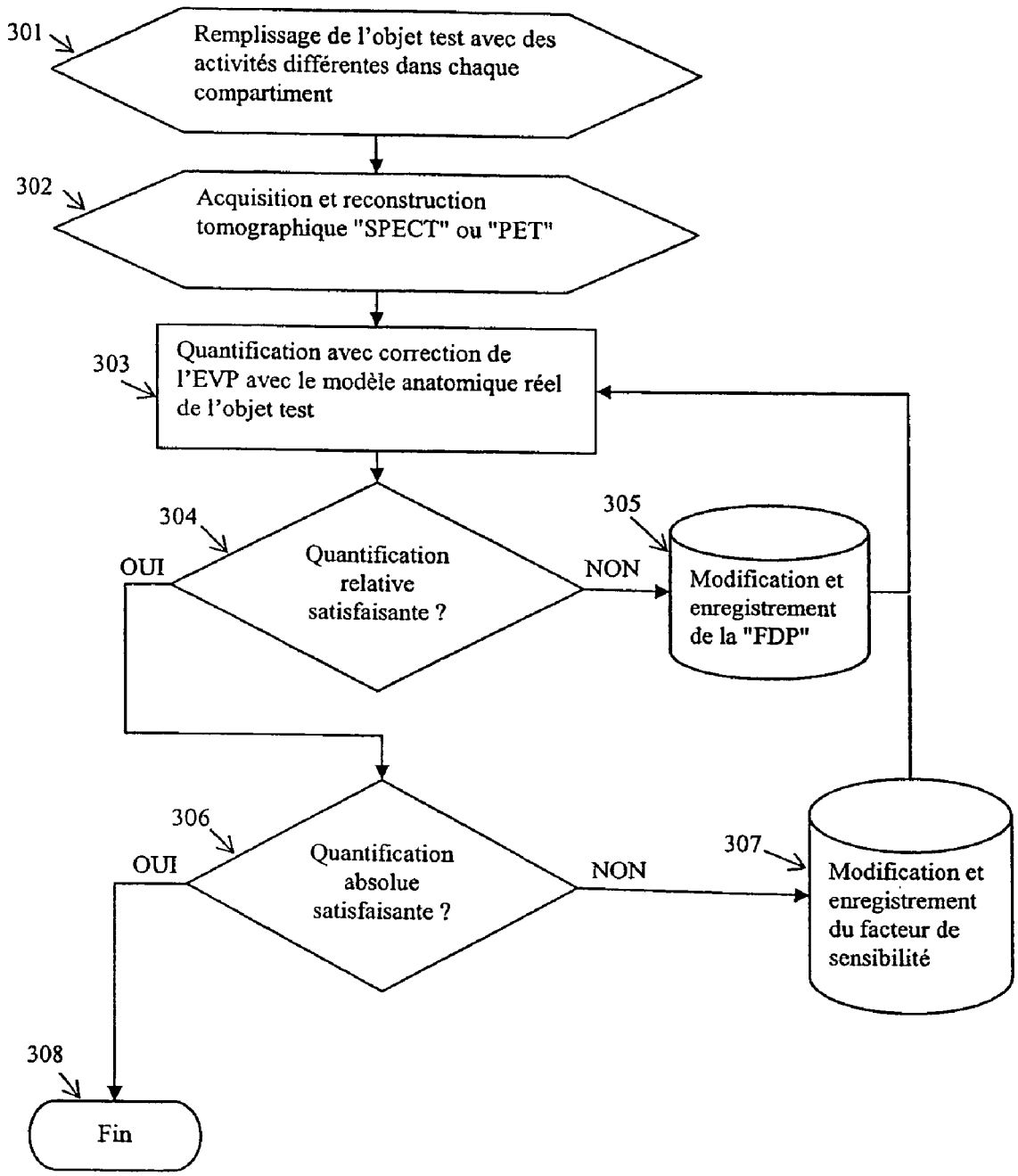
FIG. 3 is a diagram schematically illustrating the chief steps of calibrating a detection and treatment chain by means of a test object.

At the step marked 304, an adequation test of the results of the relative quantification, i.e., the relationship of the volume radioactivities of the compartments in relation to one another makes it possible to know whether the PDF (available at the end of step 102 of FIG. 1) used in the quantification process is correct: branch YES of FIG. 3. This step consists in comparisons with the pre-established thresholds.

If the result of these comparisons is negative (NO branch of FIG. 3), the PDF is modified and stored in the memory means at the step marked 305.

The quantification step 303 is then reiterated until the test at step 304 becomes positive: the YES branch.

A second test, at step 306, makes it possible to know whether the absolute volume activity given by the quantification process (results stored at the end of step 303) are close to the real values injected into the "anthropomorphic phantom" of step 301: YES branch of FIG. 3. This step consists also in comparisons with pre-established thresholds.

If the result of these comparisons is negative (NO branch of FIG. 3), the "sensitivity" factor of the detection chain is modified and stored in the memory means at step 307.

Then the quantification step 303 is repeated until the values obtained are near those expected (positive test): YES branch of FIG. 3, leading to the end of the calibration process or step 308. The data thus obtained are used to determine the point dispersion function or PDF.

The sensitivity factor is a factor of standardization of the SPECT or PET data which can be used in the eventual correction step 104 (FIG. 1) when the quantification process (steps 101 to 115 of FIG. 1) is used to furnish (step 114 of FIG. 1) absolute values of volume activities.

The calibration process that has just been described in regard to FIG. 3 guarantees the accuracy of the values measured, which makes it possible to establish normalcy values independently of the physical acquisition system used.

Figure 4:
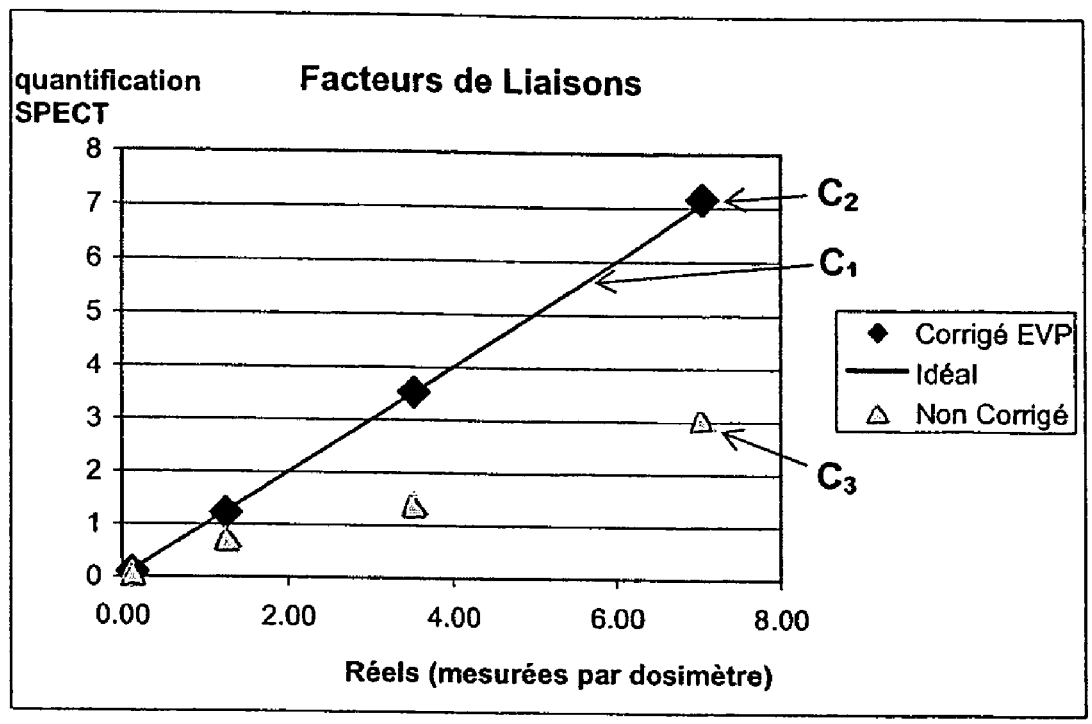
FIGS. 4 and 5 are examples of curves illustrating steps of the process of FIG. 1.
Figure 5:
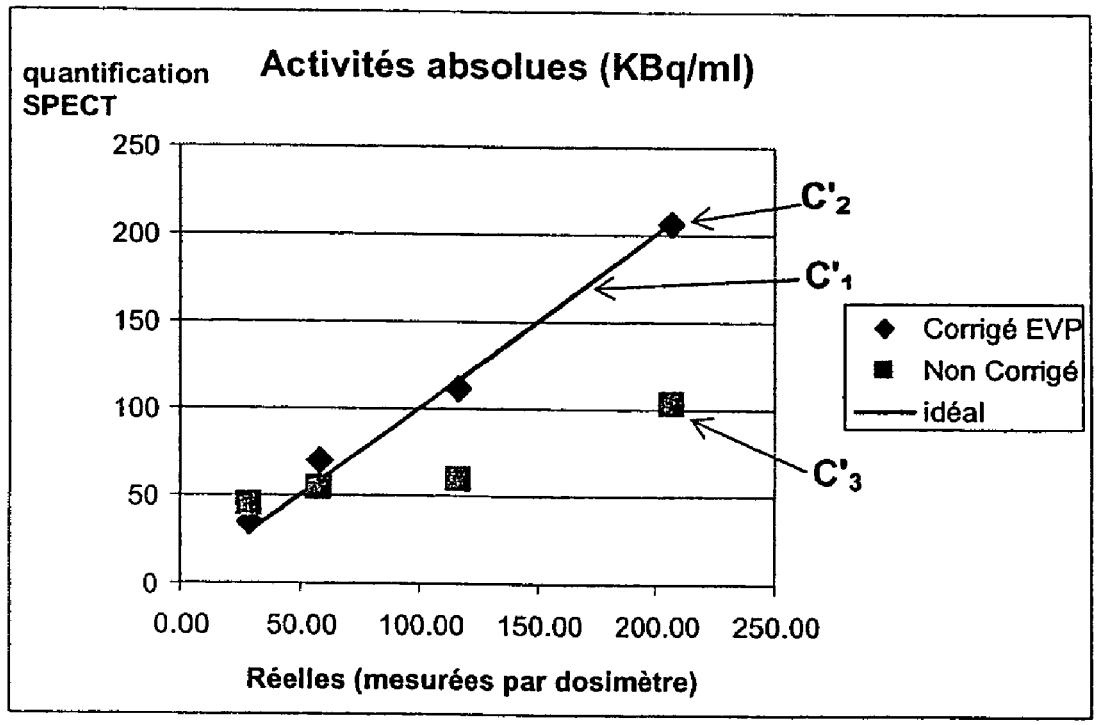

To be concrete, two examples of sets of curves have been represented in FIGS. 4 and 5:

FIG. 4 illustrates the effect of the calibration of the PDF on the measurements relating to activity (connection factor curves): curves $C_1$ to $C_3$. The liaison factor is calculated classically by the (S–O)/O where S concerns the radioactive concentration in the structure of the striatum, and O the radioactive concentration in a reference zone, here in the rest of the brain. The abscissae represent the real values of the liaison factor, calculated from the measurement of the radioactivity in the test object by means of a dosimeter, also called an activimeter, an instrument currently used in the Nuclear Imaging Clinical Services. The ordinates represent the values of the liaison factor measured in SPECT, with or without PVE correction according to the calibration process.

FIG. 5 illustrates the effect of the calibration of the PDF and of the sensitivity factor on the absolute measurements of radioactivity in the different structures of the test object, expressed in KBq/ml (absolute activities: curves $C'_1$ to $C'_3$.)

In both cases, the index 1 is associated with ideal theoretical values, index 2 with corrected values and index 3 with uncorrected values.

The first diagram (FIG. 4) is used at step 304 of FIG. 3. The second diagram (FIG. 5) is used at step 306 of FIG. 3.

Figure 6:
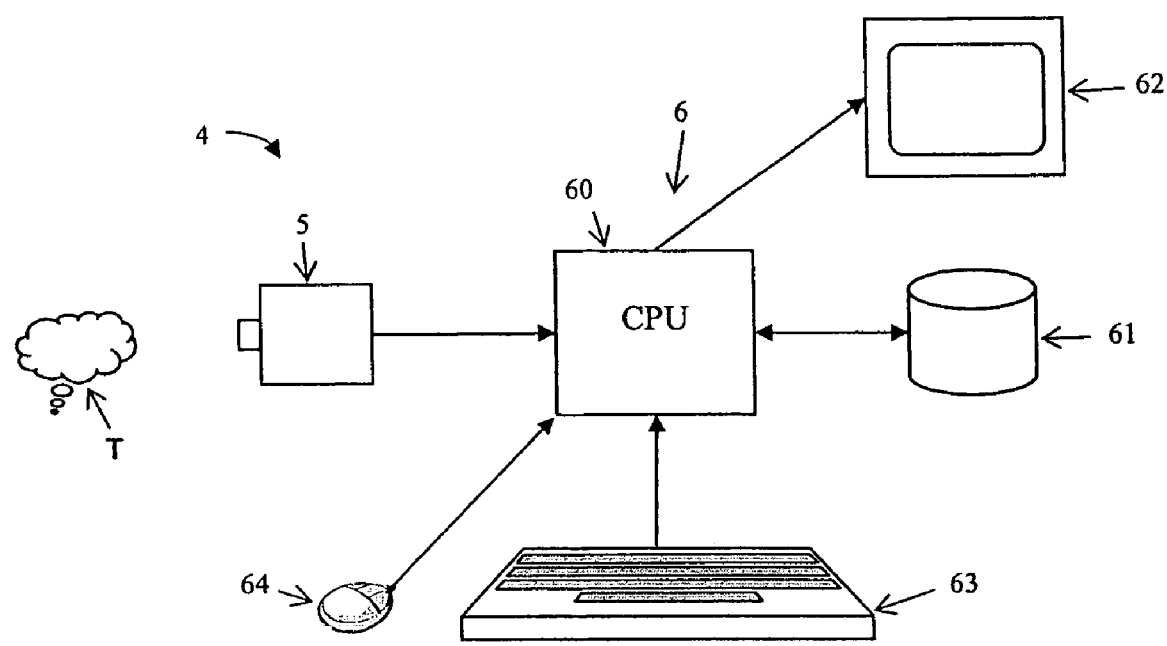
FIG. 6 illustrates schematically the architecture of the complete chain for the acquisition and processing of images for the employment of the process of the invention.

FIG. 6 shows very schematically a complete imaging system architecture making it possible to practice the method of the invention.

The imaging system 4 comprises a camera 5 for obtaining SPECT or PET images of a tissue T connected to a data processing system 6 using recorded programs. The latter comprises memory means, particularly a mass memory, for example one or more hard disks 61, a display unit, for example a cathodic screen 62, data input means: a keyboard 63, pointer means (mouse) 64, and other classical units not represented.

The camera 5 is a gamma photon detection camera. As an example, this camera is a so-called scintillation camera, with coincidence detection (in PET) or without such detection (in SPECT). Such a camera is commonly used for performing tomoscintigraphic examinations in the Nuclear Imaging Services.

The programs recorded in the mass memory means 61 or in other memory means (for example an internal read-only memory or ROM comprising, in addition to classical programs for the good operation of the data processing system (standard or proprietary, etc . . . operating system), programs specifically for the practice of the method of the invention, as it was mentioned in the description of the steps of the process, particularly for all operations performed automatically.

The display unit 62 permits particularly the display of the results at step 114 of FIG. 1.

The data entry means 63–64 can be used particularly for initializing the processes and entering configuration parameters.

By reading the foregoing it is easy to see that the invention achieves the purposes which it sets for itself.

Without repeating all the advantages, it particularly permits a very good correction of the partial volume effect or EVP in a real venue, i.e., in a hospital setting, for example. It therefore permits a reliable evaluation of the radioactivity of small structures, that is to say, a quantification of this activity without requiring either an IRM examination, or a segmentation of prior IRM images.

These advantages are mainly due to recourse to a deformable model, according to the essential one of the features of the invention.

It should be clear, however, that the invention is not limited to only the embodiments explicitly described, particularly in relation to FIGS. 1 to 6.

The invention claimed is:

1. A process of quantifying the radioactivity of a set of living tissue structures to determine the concentration of a radioactive tracer in said living tissue structures, the process comprising the steps:

(a) acquiring and reconstructing a plurality of images of the said living tissue structures in three dimensions using an imaging system comprising a detection chain and employing emission tomography and storing said plurality of three-dimensional images in the form of numerical data in a memory;

(b) generating a high resolution generic anatomical numerical model of a shape approximating said living tissue structures and storing said high resolution generic anatomical model in the form of numerical data in said memory;

(c) determining a point dispersion function of said detection chain and storing parameters characterizing said point dispersion function in the form of numerical signals in said memory;

(d) convoluting said high-resolution generic anatomical numerical model with said parameters of said point dispersion function to obtain a low resolution model of said high-resolution generic anatomical numerical model and storing said low resolution model in the form of numerical data in said memory;

(e) readjusting between said plurality of three-dimensional images and said low resolution model;

(f) estimating a match between said plurality of three-dimensional images and said low resolution model and testing said match using predetermined threshold values;

(g) performing iterative tests if the testing of said match is negative, comprising the step of deforming said high resolution generic anatomical numerical model, storing deformation of said high resolution generic anatomical numerical model in the form of numerical data in said memory, and repeating said steps (d)–(f) until the testing of said match is positive;

(h) segmentating said low resolution model in regions superimposed on said numerical data of said plurality of three dimensional images;

(i) determining the radioactivity in said plurality of three-dimensional images in segmented regions and storage the radioactivity in the form of numerical data in said memory;

(j) determining a geometric transfer matrix starting from said high resolution generic anatomical numerical model and low resolution model, and storing said geometric transfer matrix in the form of numerical data in said memory; and (k) inverting said geometric transfer matrix and multiplying inverted geometric transfer matrix by said numerical data representing the radioactivity of said segmented regions to obtain correction data of partial volume effect associated with said living tissue structures, thereby providing a quantification data of radioactive concentration within said living tissue structures.

2. The process of claim 1, further comprising the step of displaying on a visualization unit said quantification data of said radioactive concentration within said living tissue structures.

3. The process of claim 1, further comprising the step of storing said quantification data of said radioactive concentration within said living tissue structures in said memory.

4. The process of claim 1, wherein said living tissue structures comprises small dimensional structures called striata; wherein said emission tomography is a single photon computerized tomography (SPECT) or positron emission tomography (PET); and wherein the step of acquiring and reconstructing comprises the step of acquiring dopaminergic neurotransmission images of said living tissue structures.

5. The process of claim 2, wherein the step of readjusting comprises three translational operations and three rotational operations.

6. The process of claim 5, wherein the step of readjusting comprises the step performing readjustments using manual commands; and wherein the step of displaying comprises the step of displaying results of said readjustments on said visualization unit.

7. The process of claim 5, wherein the step of readjusting comprises the step automatically performing readjustments by a numerical data processing unit.

8. The process of claim 2, wherein the step of estimating comprises the step of performing match appraisal manually by visual observation on said visualization unit.

9. The process of claim 1, wherein the step of estimating comprises the step of automatically performing match appraisal in accordance with a numerical estimation of distances between images by a numerical data processing unit.

10. The process of claim 1, wherein the step deforming comprises the step of translating and/or rotating said plurality of three-dimensional images of said living tissue structures.

11. The process of claim 1, wherein the step of determining said point dispersion function comprises the step of calibrating said detection chain.

12. The process of claim 11, wherein the step of calibrating comprises the steps of:

obtaining a test object whose characteristics are substantially close to said living tissue structures in form and density, said test object comprises a plurality of compartments;

filling each compartment with a distinct radioactivity tracer of known value;

acquiring a plurality of three-dimensional images by said imaging detection chain from said compartments;

quantifying the radioactivity of said compartments by:
generating a numeric anatomical model having a shape approximating the real form of said compartments;
determining said point dispersion function, convolution, readjustment, segmentation into regions;
determining the radioactivity of said regions; and
determining a geometric transfer matrix, inversion of said geometric transfer matrix, matrix multiplication and display and/or printing of quantification data on radioactive distribution of said compartments, thereby obtaining a quantification data to correct said partial volume effect associated with said compartments, and storing said quantification data in the form of numerical data in said memory;

first testing of the results of a relative quantification by comparing the volume radioactivities of said compartments in relation to one another to determine whether said point dispersion function resulting from the step of quantifying the radioactivity of said compartments satisfy a predetermined criteria based on a comparison with predetermined thresholds;

modifying said point dispersion function to provide a modified function if the first testing is negative, storing said modified function in the form of numerical data in said memory, and repeating the steps of quantifying the radioactivity of said compartments and first testing until said first testing is positive;

second testing by comparing said known radioactivity values of said compartments with values associated with said quantification data to determine whether said quantification data satisfy predetermined criteria based on a comparison with preestablished thresholds;

modifying a sensitivity factor of said detection chain if said second testing is negative, storing said sensitivity factor in the form of numerical data in said memory means, and repeating the steps of quantifying the radioactivity of said compartments and second testing until said second testing is positive; and determining said point dispersion function from said quantification data.

13. A computer readable medium comprising code for quantifying the radioactivity of a set of living tissue structures to determine the concentration of a radioactive tracer in said living tissue structures, said code comprising instructions for:

(a) acquiring and reconstructing a plurality of images of the said living tissue structures in three dimensions using an imaging system comprising a detection chain and employing emission tomography and storing said plurality of three-dimensional images in the form of numerical data in a memory;

(b) generating a high resolution generic anatomical numerical model of a shape approximating said living tissue structures and storing said high resolution generic anatomical model in the form of numerical data in said memory;

(c) determining a point dispersion function of said detection chain and storing parameters characterizing said point dispersion function in the form of numerical signals in said memory;

(d) convoluting said high-resolution generic anatomical numerical model with said parameters of said point dispersion function to obtain a low resolution model of said high-resolution generic anatomical numerical model and storing said low resolution model in the form of numerical data in said memory;

(e) readjusting between said plurality of three-dimensional images and said low resolution model;

(f) estimating a match between said plurality of three-dimensional images and said low resolution model and testing said match using predetermined threshold values;

(g) performing iterative tests if the testing of said match is negative, said iterative tests comprising instructions for deforming said high resolution generic anatomical numerical model, storing deformation of said high resolution generic anatomical numerical model in the form of numerical data in said memory, and repeating instructions (d)–(f) until the testing of said match is positive;

(h) segmentating said low resolution model in regions superimposed on said numerical data of said plurality of three dimensional images;

(i) determining the radioactivity in said plurality of three-dimensional images in segmented regions and storing the radioactivity in the form of numerical data in said memory;

(j) determining a geometric transfer matrix starting from said high resolution generic anatomical numerical model and low resolution model, and storing said geometric transfer matrix in the form of numerical data in said memory; and (k) inverting said geometric transfer matrix and multiplying inverted geometric transfer matrix by said numerical data representing the radioactivity of said segmented regions to obtain correction data of partial volume effect associated with said living tissue structures, thereby providing a quantification data of radioactive concentration within said living tissue structures.

14. The computer medium of claim 13, wherein said living tissue structures comprises small dimensional structures called striata; wherein said emission tomography is a single photon computerized tomography (SPECT) or positron emission tomography (PET); and wherein the instructions for acquiring and reconstructing comprises an instruction for acquiring dopaminergic neurotransmission images of said living tissue structures.

15. A system for quantifying the radioactivity of a set of living tissue structures to determine the concentration of a radioactive tracer in said living tissue structures, comprising:

an emission tomography imaging system comprising a detection chain for acquiring and reconstructing a plurality of images of the said living tissue structures in three dimensions; and a data processing system for:
generating a high resolution generic anatomical numerical model of a shape approximating said living tissue structures;
determining a point dispersion function of said detection chain to obtain parameters characterizing said dispersion function;
convoluting said high-resolution generic anatomical numerical model with said parameters of said point dispersion function to obtain a low resolution model of said high-resolution generic anatomical numerical model;
readjusting between said plurality of three-dimensional images and said low resolution model;
estimating a match between said plurality of three-dimensional images and said low resolution model and testing said match using predetermined threshold values;
if the testing of said match is negative, performing iterative tests comprising deforming said high resolution generic anatomical numerical model to provide deformed high resolution model and wherein said data processing system is operable to convulute, readjust and estimate based on said deformed high resolution model until the testing of said match is positive;
segmentating said low resolution model in regions superimposed on said numerical data of said plurality of three dimensional images;
determining the radioactivity in said plurality of three-dimensional images in segmented regions;
determining a geometric transfer matrix starting from said high resolution generic anatomical numerical model and low resolution model
inverting said geometric transfer matrix and multiplying inveted geometric transfer matrix by said numerical data representing the radioactivity of said segmented regions to obtain correction data of partial volume effect associated with said living tissue structures, thereby providing a quantification data of radioactive concentration within said living tissue structures.

16. The system of claim 15, further comprising a memory for storing the following in the form of numerical data: said plurality of three-dimensional images, said high resolution generic anatomical model, said parameters characterizing said point dispersion function, said low resolution model, deformation of said high resolution generic anatomical numerical model, the radioactivity, said geometric transfer matrix.

17. The system of claim 15, wherein said living tissue structures comprises small dimensional structures called striata; wherein said emission tomography is a single photon computerized tomography (SPECT) or positron emission tomography (PET); and wherein said data processing system is operable to acquire dopaminergic neurotransmission images of said living tissue structures.

* * * * *